United States Patent [19]

Anderson et al.

[11] Patent Number: 4,912,230

[45] Date of Patent: Mar. 27, 1990

[54] PROCESS FOR STEREOCHEMICALLY INVERTING A HYDROXY FUNCTION OF AN ESTER BY A MODIFIED MITSUNOBU REACTION PROCESS

[75] Inventors: Neal G. Anderson; Christopher M. Cimarusti, both of Somerset; David A. Lust, Roosevelt, all of N.J.

[73] Assignee: E. R. Squibb & Sons, Inc., Princeton, N.J.

[21] Appl. No.: 245,086

[22] Filed: Sep. 16, 1988

[51] Int. Cl.$^4$ .......................................... C07D 207/00
[52] U.S. Cl. ..................................................... 548/533
[58] Field of Search ........................................ 548/533

[56] References Cited

PUBLICATIONS

Noller, Textbook of Organic Chemistry, W. B. Saunders Co., Philadelphia, 1966, pp. 173, 226.

D. L. Hughes, R. A. Reamer, J. J. Bergan, and E. J. J. Grabowski, in Journal of the American Chemical Society (1988), vol. 110, No. 19, pp. 6487–6491.

Oyo Mitsunobu, in *Synthesis* (1981), pp. 1–28, "The Use of Diethyl Azodicarboxylate and Triphenylphosphine in Synthesis and Transformation of Natural Products".

Amos B. Smith, III et al., in *Tetrahedron Letters* (1986), vol. 27, No. 48, pp. 5813–5816, "An Efficient Synthesis of Glycosyl Esters Exploiting the Mitsunobu Reaction".

Igor Galynker et al., in *Tetrahedron Letters* (1982), vol. 23, No. 43, pp. 4461–4464, "A Simple Method for Tosylation with Inversion".

J. R. Falck et al., in *Tetrahedron Letters* (1984), vol. 25, No. 23, pp. 2443–2446, "Enantiospecific Synthesis of Methyl 11,12– and 14,15–Epoxyeicosatrienoate".

Patrick Rollin, in *Synthetic Communications* (1986), 16(6), 611–616, "Nucleophilic Inversions of a Chiral Alcohol Medicated by Zinc Salts".

*Primary Examiner*—Mary C. Lee
*Assistant Examiner*—Robert C. Whittenbaugh
*Attorney, Agent, or Firm*—Timothy J. Gaul

[57] ABSTRACT

A process is provided for inverting a hydroxy function of a L-trans-hydroxy proline derivative to the corresponding L-cis-hydroxy proline sulfonate by a Modified Mitsunobu reaction process.

10 Claims, No Drawings

PROCESS FOR STEREOCHEMICALLY INVERTING A HYDROXY FUNCTION OF AN ESTER BY A MODIFIED MITSUNOBU REACTION PROCESS

FIELD OF THE INVENTION

The present invention relates to a modified Mitsunobu Reaction process for stereochemically converting a hydroxy function to form the epimeric sulfonate and more particularly to converting the hydroxy function of a L-trans-hydroxy proline derivative to the corresponding L-cis-hydroxy proline sulfonate.

BACKGROUND OF THE INVENTION

The preparation of angiotensin converting enzyme inhibitors such as fosinopril involves a complicated series of steps. The stereospecificity of the intermediate products is very important and often difficult to control. One set of the series of steps used to synthesize involves the conversion of N-benzoyl-trans-4-hydroxy-L-proline methyl ester (See A below) to cis-mesylate methyl ester (See B below), via the following lactonization process:

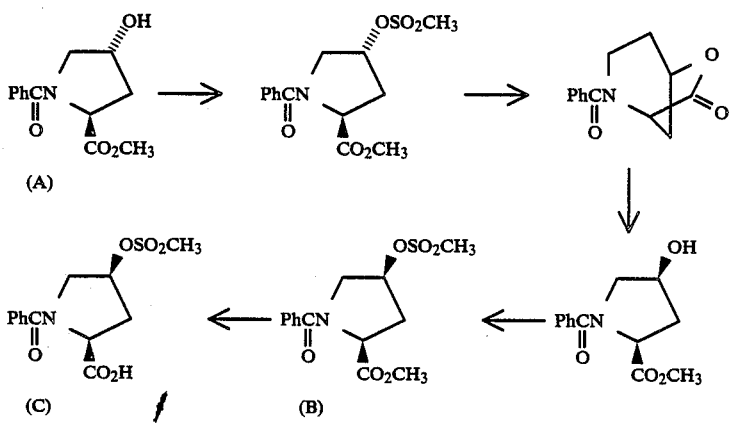

The mesylate (C) is a useful intermediate to fosinopril. However, the process requires several steps and is difficult. Using several steps could lead to poor control of the stereochemical integrity of the mesylate acid resulting in cis and trans epimers being formed. Poor stereochemical control creates a substantial problem since a subsequent Friedal-Crafts alkylation also proceeds with inversion. Inefficiency in either step could ultimately lead to cyclohexyl isomers of fosinopril sodium and subsequent purification problems.

An attempt was therefore made to simplify the procedure using the Mitsunobu process as taught in Synthesis (1981) p 1–28. However, the conventional Mitsunobu process proved too cumbersome to be of commercial value. The process has been modified to better meet the needs of a commercial application.

The invention provides for the coupling of a hydroxy proline derivative with a sulfonic acid by preparing an ammonium sulfonate in situ, instead of utilizing a discrete preparation of a zinc sulfonate. This eliminates one step of the Mitsunobu process as taught by Galynker and Still in Tetrahedron Letters (1982), Vol. 23, No. 43, pp 4461–4464. Also the majority of the reagent by-products can now be removed by filtration because, unexpectedly, a 1:1 by-product complex forms and crystallizes upon partial acidification. This eliminates the cumbersome chromotagraphy process generally required. Consequently, the new process simplifies the purification procedure tremendously.

SUMMARY OF THE INVENTION

In accordance with the present invention, there is provided a method to invert the hydroxy function of a L-trans-hydroxy proline derivative to the corresponding L-cis-hydroxy proline sulfonate comprising the steps of: (a) reacting an hydroxy ester with a sulfonic acid, a trivalent phosphorous compound, an azocompound and a trialkylamine, in the presence of an inert, organic solvent; (b) hydrolyzing and partially acidifying the reaction mixture; (c) recovering the crystallized by-product complex; (d) acidifying the filtrate; and, (e) recovering the crystallized L-cis-hydroxy proline sulfonate.

DETAILED DESCRIPTION OF THE INVENTION

In broadest terms, the invention involves a simplified process to invert the hydroxy function of a L-trans-hydroxy proline derivative to the corresponding L-cis-hydroxy proline sulfonate by a modified Mitsunobu reaction. The process involves an hydroxy proline derivative, an azocompound, a trivalent phosphorus compound (generally triphenylphosphine), a sulfonic acid (generally methanesulfonic acid), and a source for the formation of an organic salt of the sulfonic acid (generally trialkylamine and more particularly triethylamine). The by-products of the reaction are the phosphine oxide and the reduced azo derivative (a hydrazine derivative) which form a 1:1 by-product complex which crystallizes upon partial acidification.

The Mitsunobu process provides for formation of the epimeric ester of a secondary alcohol. Typically, the formation of a zinc salt of the sulfonic acid is a required step. However, the process proved too cumbersome to be useful for commercial production of a product. The present invention does not require the prior formation of the zinc salt from the sulfonic acid, but rather teaches the use of a trialkylamine in conjunction with the sulfonic acid.

Consequently, the steps of preparation and isolation of the zinc salt has been eliminated. Similarly, under the reaction conditions chosen, and with the preferred reagents, the use of chromatography to remove the by-products has been eliminated.

Cis-hydroxy proline sulfonate has been produced with very low levels of trans-hydroxy proline sulfonate contamination by a simple two step process.

The Modified Mitsunobu Process is outlined in Reaction Sequence I and the subsequent hydrolysis and acidification step is outlined in Reaction Sequence II.

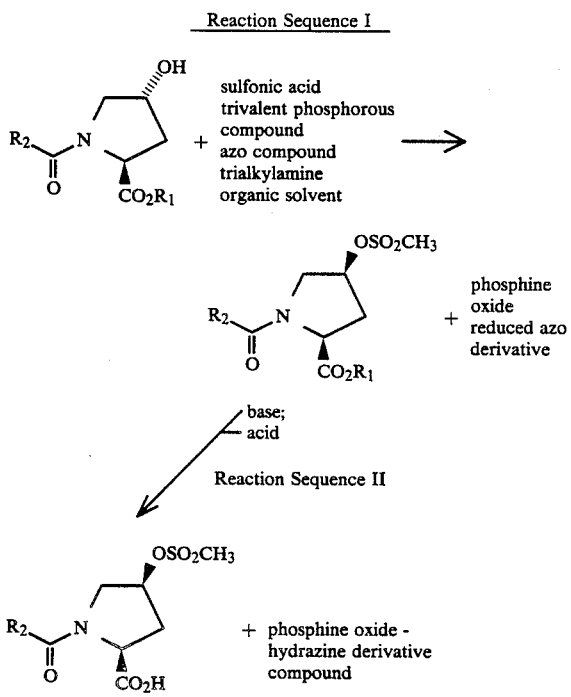

As shown in Reaction Scheme I, a proline derivative, wherein $R_1$, is an alkyl group having 1 to 10 carbon atoms and $R_2$ is phenyl, or alkyl- or halo-substituted phenyl, is reacted with a sulfonic acid such as alkyl, or aryl, or substituted aryl sulfonic acids, a trivalent phosphorous compound, such as triphenylphosphine, an azocompound such as dialkylazo dicarboxylate, and a source for the formation of an organic salt such as trialkylamines, wherein the alkyl group has 1 to 10 carbon atoms, in the presence of an inert organic solvent, such as toluene. The temperature of the reaction can range from about 40° C. to about 100° C. and preferably is about 80° C. The reaction time can range from about 32 hours to about 5 hours and preferably is from 2 hours to about 5 hours depending on the temperature of the reaction. A cis-sulfonat carboxylic acid ester forms and the by-products of the reaction are a phosphine oxide and a reduced azo derivative (a hydrazine derivative). In Reaction Sequence II the cis-sulfonate carboxylic acid ester, which is not isolated, is hydrolyzed and partially acidified allowing a 1:1 by-product complex, (phosphine oxide - hydrazine derivative) to crystallize. The complex is removed by filtering. The biphasic filtrate is separated, the aqueous phase is washed with a suitable solvent, such as toluene, acidified and cis-sulfonate carboxylic acid crystals are collected by filtration. In the preferred embodiment of the invention, N-benzoyl-trans-4-hydroxy-L-proline methyl ester is reacted with methanesulfonic acid, triphenylphosphine, diisopropyl azodicarboxylate and triethylamine to form cis-mesylate methyl ester, phosphine oxide and a reduced azo derivative. The reaction mixture is treated with aqueous sodium hydroxide and then partially acidified with HCl. The crystallized by-product complex, triphenylphosphine oxide-diisopropyl hydrazinodicarboxylate in a 1:1 ratio, is removed by filtering. The biphasic filtrate is separated and the aqueous phase is washed with toluene, and acidified. Cis-mesylate carboxylic acid crystals form and are collected by filtration.

The following example illustrates the particular method for preparing compounds in accordance with this invention. The example is illustrative and is not meant to be read as limiting the scope of the invention as it is defined in the appended claims.

EXAMPLE 1

To a 1000 mL 5-necked round-bottomed flask, fitted with mechanical paddle stirrer, reflux condenser with $CaSO_4$ drying tube, and thermostatted heating mantle, were added 250 mL of toluene (92.14 MW, 0.867 g/ml), 7.78 mL of methanesulfonic acid (96.19 MW, 0.12 Moles, 1.483 g/ml) and 16.73 mL of triethylamine (101.19 MW, 0.12 Moles, 0.726 g/mL), with the temperature rising to 35°–40° C. The reaction was continued with the addition of 32.79 g of triphenylphosphine ("TPP", 262.2 MW, 0.125 Moles), and 24.93 g of N-benzoyl-trans-4-hydroxy-L-proline methyl ester. To the suspension was then added 24.38 mL of diisopropyl azodicarboxylate ("DIAD", 202.21 MW, 0.125 Moles, 1.027 g/mL), the temperature rising to ca. 55° C.

The suspension was then heated rapidly to 80° C.+2° C., and maintained at 80° C.+2° C. for 2–5 hours, until the reaction was complete as determined by HPLC analysis.

The intermediate mesylate methyl esters are formed in a ratio of ≧97:3 cis:trans.

The orange-brown solution was cooled to 20°–30° C., and quenched with the addition of 75 mL $H_2O$. The biphasic mixture was then treated with 15.0 mL of 10 M NaOH, and stirred vigorously.

The resulting triphasic mixture was then acidified to pH 6–7 with about 11 mL of concentrated HCl, and cooled to 0°–5° C.

The by-product was filtered off, and washed with 35 mL of 0°–5° C. water (cake volumes about 75 –90 mL). The filtrates were combined.

Vacuum drying at 40° C. returned 45.14–50.77 g of solid, mp ca. 113°–115° C. This material was composed of triphenylphosphine oxide and reduced diisopropyl azodicarboxylate in the ratio of ca. 1:1 as shown by NMR analysis.

The biphasic filtrate was warmed to 20–25° C. and the phases were separated. The slightly opaque, light yellow aqueous phase was washed with 50 mL of toluene, and the organic phases were combined.

The rich aqueous phase was warmed to about 45° C.–55° C., and acidified to about pH 4.0 with 2–3 mL of concentrated HCl. The solution was then cooled to initiate crystallization and seeded with 50 mg of cis-mesylate acid. The developing suspension is held at the crystallization temperature for about 30 minutes.

The slurry was acidified over a time period of about 10–30 minutes to pH of about 1.0 using 7–8 mL of concentrated HCl. The suspension was held at 50° C. for 30 minutes.

The suspension was then cooled to about 0°–5° C. over 30–60 minutes, and held there for ca. 1 hour. The cake was washed with two 75 mL portions of 0°–5° C. $H_2O$, or until negligible amounts of chloride were being eluted in the filtrates.

Vacuum drying at 40° C. returned 24.97–26.85 g of cis-mesylate acid, for an uncorrected yield of 79.7–85.7 M%.

Analysis of the product shows, on HPLC analysis, that there is generally less than 0.1% of isomeric impurities. The final product had a melting point temperature of ca. 168°–171° C.

What is claimed is:

1. A method to invert the hydroxy function of a L-trans-hydroxy proline derivative to the corresponding L-cis-hydroxy proline sulfonate, which method comprises: (a) reacting an hydroxy ester with a sulfonic acid, a trivalent phosphorous compound, an azocompound and a trialkylamine in the presence of an organic solvent; (b) hydrolyzing and partially acidifying the reaction mixture; (c) recovering the crystallized by-product complex; (d) acidifying the filtrate; (e) recovering the crystallized L-cis-hydroxy proline sulfonate.

2. The method as defined in claim 1 wherein the proline derivative is

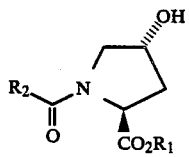

and $R_1$ is an alkyl group having 1 to 10 carbon atoms and $R_2$ is phenyl, or alkyl- or halosubstituted phenyl.

3. The method as defined in claim 1 wherein the sulfonic acid is an alkyl sulfonic acid, or an aryl or substituted aryl sulfonic acid.

4. The method as defined in claim 1 wherein the trivalent phosphorous compound is triphenylphosphine.

5. The method as defined in claim 1 wherein the azocompound is dialkyl azodicarboxylate.

6. The method as defined in claim 1 wherein the trialkylamine is triethylamine.

7. The method as defined in claim 1 wherein the temperature range of the reaction in step (a) is between 40° C. to 100° C. for a reaction time of from 32 hours to 2 hours.

8. The method as defined in claim 9 wherein the temperature is about 80° C. and the reaction time is between 2–5 hours.

9. A method of preparing the epimeric sulfonate of the 4-hydroxy function of N-benzoyl trans-4-hydroxy-L-proline methyl ester by reacting the ester with a sulfonic acid, a trivalent phosphorous compound, an azocompound, and trialkylamine in an inert organic solvent, hydrolyzing and partially acidifying the reaction mixture, filtering out the resulting by-product complex, washing the filtrate with an inert organic solvent, acidifying the filtrate, and filtering the resulting cis-sulfonate carboxylic acid.

10. The method as defined in claim 9 wherein the sulfonic acid is methanesulfonic acid, the trivalent phosphorous compound is triphenylphosphine the azocompound is diisopropyl azodicarboxylate, the trialkylamine is triethylamine and the inert organic solvent is toluene and the final product is cis-methane sulfonate carboxylic acid.

* * * * *